(12) United States Patent
Dunning et al.

(10) Patent No.: US 9,192,439 B2
(45) Date of Patent: Nov. 24, 2015

(54) METHOD OF MANUFACTURING A SURGICAL INSTRUMENT

(71) Applicant: COVIDIEN LP, Mansfield, MA (US)

(72) Inventors: James E. Dunning, Lafayette, CO (US); Joseph D. Brannan, Erie, CO (US); William O. Reid, Jr., Frederick, CO (US); Darion R. Peterson, Boulder, CO (US); Kaylen J. Haley, Westminster, CO (US); Richard A. Willyard, Longmont, CO (US); Kenlyn S. Bonn, Lakewood, CO (US)

(73) Assignee: Covidien LP, Mansfield, MA (US)

( * ) Notice: Subject to any disclaimer, the term of this patent is extended or adjusted under 35 U.S.C. 154(b) by 236 days.

(21) Appl. No.: 13/908,555

(22) Filed: Jun. 3, 2013

(65) Prior Publication Data

US 2014/0000098 A1    Jan. 2, 2014

Related U.S. Application Data

(60) Provisional application No. 61/666,089, filed on Jun. 29, 2012.

(51) Int. Cl.
*A61B 17/32* (2006.01)
*A61B 18/18* (2006.01)
*A61B 17/00* (2006.01)
*A61B 18/00* (2006.01)

(52) U.S. Cl.
CPC ... *A61B 18/1815* (2013.01); *A61B 2017/00106* (2013.01); *A61B 2018/00577* (2013.01); *A61B 2018/00642* (2013.01); *A61B 2018/1869* (2013.01); *Y10T 29/49016* (2015.01)

(58) Field of Classification Search
CPC ............... A61B 2017/29; A61B 2017/2901; A61B 2017/2902; B25C 5/00; Y10T 29/49002
See application file for complete search history.

(56) References Cited

U.S. PATENT DOCUMENTS

| D223,367 | S | 4/1972 | Kountz |
| D263,020 | S | 2/1982 | Rau, III |
| D266,842 | S | 11/1982 | Villers et al. |

(Continued)

FOREIGN PATENT DOCUMENTS

| CN | 1103807 A | 6/1995 |
| DE | 390937 C | 3/1924 |

(Continued)

OTHER PUBLICATIONS

International Search Report from corresponding PCT/US2013/044774 dated Nov. 4, 2013.

(Continued)

*Primary Examiner* — Carl Arbes

(57) ABSTRACT

A method of manufacturing a surgical instrument includes charging a first component to a first voltage, charging a second component to a second voltage such that a pre-determined voltage differential is established between the first and second components, axially moving at least one of the first and second components relative to the other, monitoring an electrical characteristic to determine whether an axial distance between the first and second components is equal to a target axial distance, and retaining the first and second components in fixed position relative to one another once the axial distance between the first and second components is equal to the target axial distance.

16 Claims, 8 Drawing Sheets

(56) References Cited

U.S. PATENT DOCUMENTS

| | | | |
|---|---|---|---|
| D278,306 S | 4/1985 | McIntosh | |
| D295,893 S | 5/1988 | Sharkany et al. | |
| D295,894 S | 5/1988 | Sharkany et al. | |
| D354,218 S | 1/1995 | Van de Peer | |
| 5,769,086 A * | 6/1998 | Ritchart et al. | 600/566 |
| D424,693 S | 5/2000 | Pruter | |
| D424,694 S | 5/2000 | Tetzlaff et al. | |
| D425,201 S | 5/2000 | Tetzlaff et al. | |
| 6,086,544 A * | 7/2000 | Hibner et al. | 600/564 |
| D449,886 S | 10/2001 | Tetzlaff et al. | |
| D457,958 S | 5/2002 | Dycus et al. | |
| D457,959 S | 5/2002 | Tetzlaff et al. | |
| 6,506,189 B1 | 1/2003 | Rittman, III et al. | |
| 6,652,520 B2 | 11/2003 | Moorman et al. | |
| D487,039 S | 2/2004 | Webster et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| 7,160,292 B2 | 1/2007 | Moorman et al. | |
| D541,418 S | 4/2007 | Schechter et al. | |
| D541,938 S | 5/2007 | Kerr et al | |
| 7,276,061 B2 | 10/2007 | Schaer et al. | |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| 8,028,885 B2 * | 10/2011 | Smith et al. | 227/179.1 |
| 8,059,059 B2 | 11/2011 | Bonn | |
| 8,069,553 B2 | 12/2011 | Bonn | |
| 8,118,808 B2 | 2/2012 | Smith et al. | |
| 8,361,062 B2 | 1/2013 | Bonn | |
| D681,810 S | 5/2013 | Decarlo | |
| 2001/0008966 A1 | 7/2001 | Arndt et al. | |
| 2004/0054299 A1* | 3/2004 | Burdorff et al. | 600/564 |
| 2006/0095027 A1 | 5/2006 | Eggers | |
| 2007/0203551 A1 | 8/2007 | Cronin et al. | |
| 2009/0209990 A1* | 8/2009 | Yates et al. | 606/169 |
| 2009/0295674 A1 | 12/2009 | Bonn | |
| 2011/0054459 A1 | 3/2011 | Peterson | |
| 2011/0056069 A1 | 3/2011 | Bonn | |
| 2011/0118724 A1 | 5/2011 | Turner et al. | |
| 2011/0204119 A1* | 8/2011 | McCuen | 227/175.1 |
| 2011/0213352 A1 | 9/2011 | Lee et al. | |
| 2011/0238055 A1 | 9/2011 | Kim et al. | |
| 2012/0042506 A1 | 2/2012 | Bonn | |
| 2012/0110834 A1 | 5/2012 | Smith et al. | |
| 2012/0161786 A1 | 6/2012 | Brannan | |
| 2012/0172863 A1 | 7/2012 | Brannan | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0185810 A1 * | 7/1986 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1 159 926 A2 | 12/2001 |
| EP | 2044890 A1 * | 4/2009 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 11/1964 |
| SU | 401367 A1 | 10/1973 |
| SU | 727201 A2 | 4/1980 |
| WO | 00/36985 A2 | 6/2000 |
| WO | 2010/035831 A1 | 4/2010 |

OTHER PUBLICATIONS

LigaSureTM Vessel Sealing System, the Seal of Confidence in General, Gynecologic, Urologic, and Laparoscopic Surgery, Sales/Product Literature, Jan. 2004.

(56) References Cited

OTHER PUBLICATIONS

Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'L Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-13 Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993; Roger A. Stern.
U.S. Appl. No. 08/483,742, filed Jun. 7, 1995; Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.

(56) References Cited

OTHER PUBLICATIONS

Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedance" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Joseph D. Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.

(56) References Cited

OTHER PUBLICATIONS

U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.

\* cited by examiner

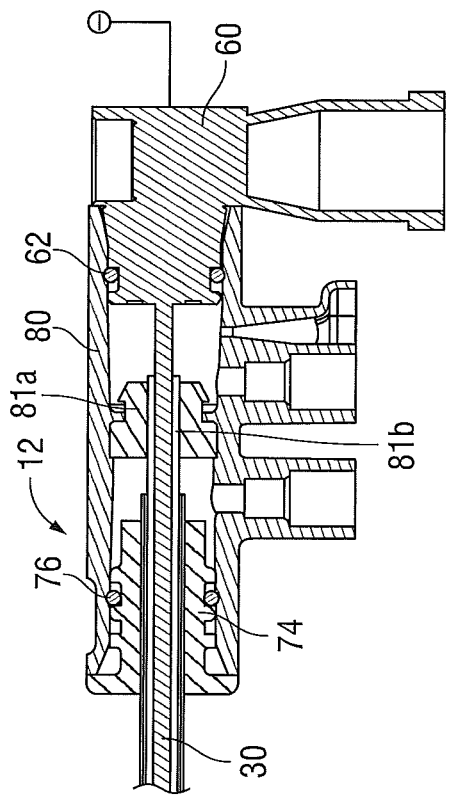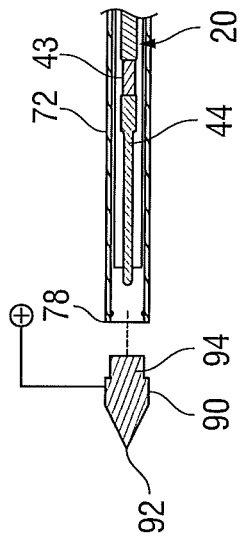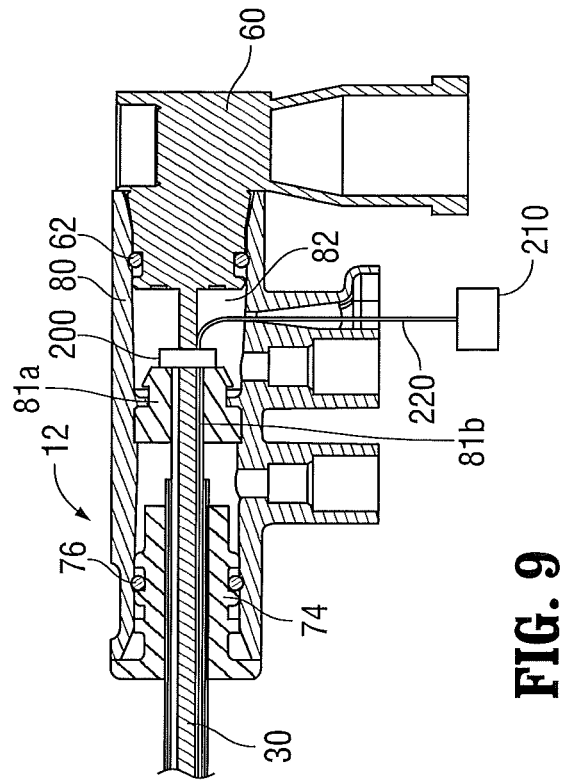
FIG. 8
FIG. 9

METHOD OF MANUFACTURING A SURGICAL INSTRUMENT

CROSS REFERENCE TO RELATED APPLICATION

The present application claims the benefit of and priority to U.S. Provisional Application Ser. No. 61/666,089, filed on Jun. 29, 2012, the entire contents of which are incorporated herein by reference.

BACKGROUND

Technical Field

The present disclosure relates to surgical instruments and, more particularly, to microwave antenna probes for treating tissue, e.g., ablating tissue, and methods of manufacturing such microwave antenna probes.

Background of Related Art

Treatment of certain diseases requires destruction of malignant tissue growths, e.g., tumors. It is known that tumor cells denature at elevated temperatures that are slightly lower than temperatures injurious to surrounding healthy cells. Known treatment methods, such as hyperthermia therapy, are utilized to heat tumor cells above the temperature necessary to destroy the tumor cells, while maintaining adjacent healthy cells at lower temperatures to avoid irreversible damage to the surrounding healthy cells. Such methods typically involve applying electromagnetic radiation to heat tissue, e.g., to ablate and/or coagulate tissue. In particular, microwave energy is used to ablate and/or coagulate tissue to denature or kill cancerous cells. There are several types of microwave antenna probes, e.g., monopole probes and dipole probes, that are currently used to radiate microwave energy generally perpendicularly from the axis of the probe to treat adjacent tissue.

SUMMARY

As used herein, the term "distal" refers to the portion that is being described which is further from a user, while the term "proximal" refers to the portion that is being described which is closer to a user. Further, to the extent they are consistent with one another, any of the aspects described herein may be used in conjunction with any of the other aspects described herein.

A method of manufacturing a surgical instrument provided in accordance with aspects of the present disclosure generally includes charging a first component to a first voltage, charging a second component to a second voltage such that a pre-determined voltage differential is established between the first and second components, axially moving one or both of the first and second components relative one another, monitoring an electrical characteristic to determine whether an axial distance between the first and second components is equal to a target axial distance, and retaining the first and second components in fixed position relative to one another once the axial distance between the first and second components is equal to the target axial distance.

In one aspect, the voltage differential between the first and second components is monitored to determine whether electrical discharge has occurred. When electrical discharge occurs, the axial distance between the first and second components is equal to the target axial distance.

In another aspect, a decrease in the voltage differential between the first and second components is monitored. A decrease in voltage differential indicates the occurrence of electrical discharge between the first and second components.

In another aspect, the pre-determined voltage differential is selected in accordance with the target axial distance between the first and second components.

In yet another aspect, conductivity and/or resistivity between the first and second components is monitored to determine the axial distance between the first and second components. In such an aspect, the first and second components may be immersed in a fluid having a pre-determined conductivity and/or pre-determined resistivity. As such, using the voltage differential between the first and second components, the pre-determined conductivity and/or pre-determined resistivity, and the monitored conductivity and/or resistivity between the first and second components, the axial distance between the first and second components can be determined.

In still another aspect, the target axial distance is determined empirically. Alternatively, the target axial distance may be determined experimentally.

In yet another aspect, the surgical instrument includes a microwave probe having a radiating portion and a trocar. The radiating portion and the trocar, e.g., the first and second components, are configured to be spaced-apart by the target axial distance.

In still yet another embodiment, the steps of axially moving the component(s), monitoring the electrical characteristic, and retaining the first and second components, are incorporated into an automated feedback system.

Another method of manufacturing a surgical instrument provided in accordance with aspects of the present disclosure generally includes providing a first component and a second component, axially moving the first component and/or the second component relative to one another, sensing a characteristic of energy to determine whether an axial distance between the first and second components is equal to a target axial distance, and retaining the first and second components in fixed position relative to one another once the axial distance between the first and second components is equal to the target axial distance.

In one aspect, the capacitance and/or the inductance between the first and second components is sensed to determine the axial distance between the first and second components.

In another aspect, one or more magnetic fields are applied to the surgical instrument. In such an aspect, characteristics of the magnetic field are sensed to determine the axial distance between the first and second components.

In still another aspect, an acoustic response is sensed to determine whether the axial distance between the first and second components is equal to the target axial distance. In such an aspect, the acoustic response is sensed in response to an acoustic excitation signal emitted generally towards the first and second components.

In yet another aspect, the target axial distance is determined empirically. Alternatively, the target axial distance may be determined experimentally.

In still yet another aspect, the surgical instrument includes a microwave probe having a radiating portion and a trocar. The radiating portion and the trocar, e.g., the first and second components, are configured to be spaced-apart by the target axial distance.

In another aspect, the steps of axially moving the component(s), sensing the characteristic of energy, and retaining the first and second components, are incorporated into an automated feedback system.

BRIEF DESCRIPTION OF THE DRAWINGS

Various aspects of the present disclosure are described herein with reference to the drawings wherein like reference numerals identify similar or identical elements:

FIG. 8 is a longitudinal, cross-sectional view illustrating assembly of the microwave antenna probe of FIG. 2 in accordance with aspects of the present disclosure;

FIG. 9 is a longitudinal, cross-sectional view illustrating assembly of the microwave antenna probe of FIG. 2 in accordance with other aspects of the present disclosure;

DETAILED DESCRIPTION

Figure 1:
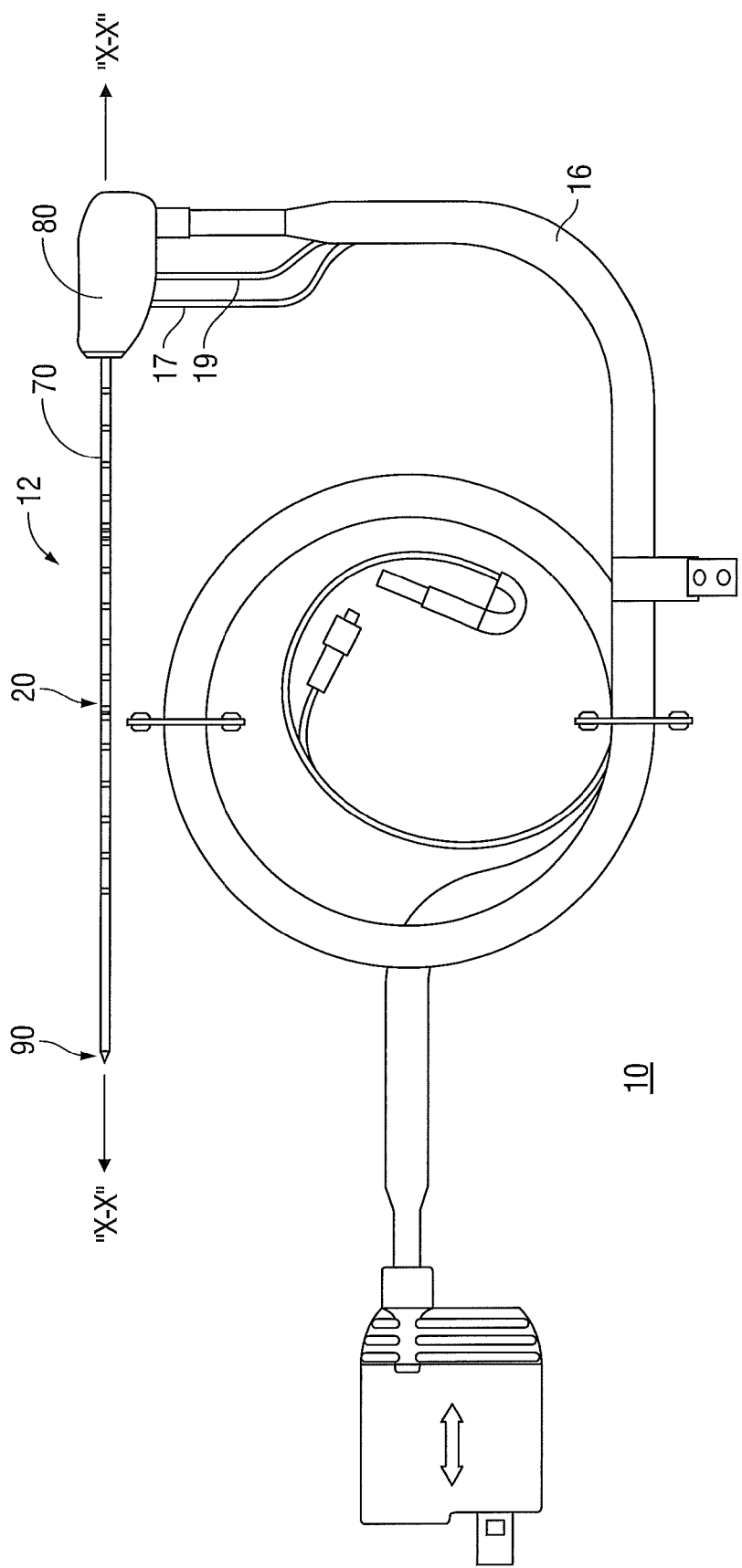
FIG. 1 is a side view of a microwave ablation system provided in accordance with the present disclosure.
Figure 2:
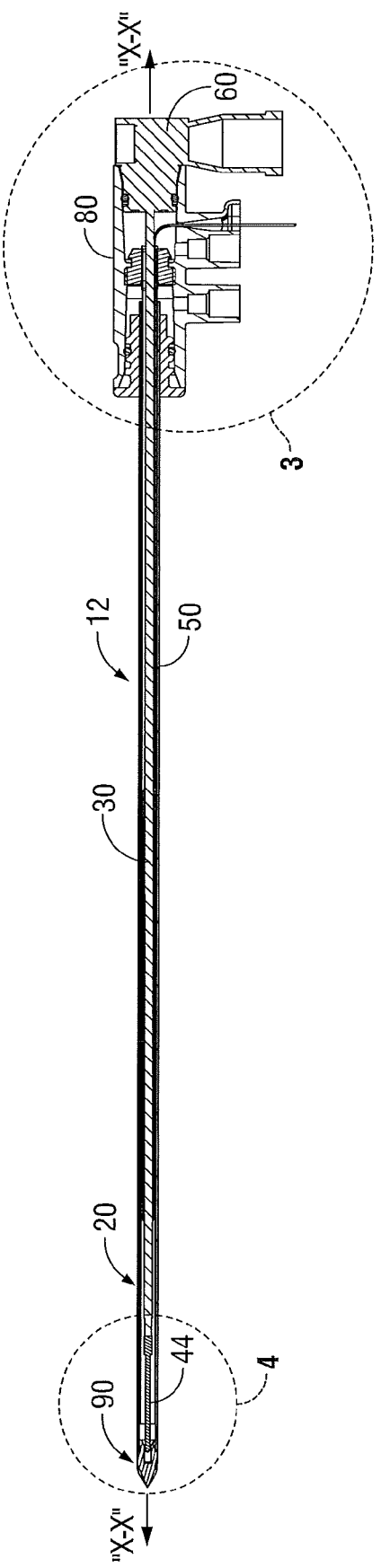
FIG. 2 is a longitudinal, cross-sectional view of a microwave antenna probe of the microwave ablation system of FIG. 1.

It has been found that, with respect to surgical instruments configured to apply energy to tissue to treat tissue, proper spacing between the energy radiating portion or portions and other components of the instrument helps facilitate optimal performance of the instrument. With respect to microwave ablation probes in particular, is has been found that proper axial spacing between the distal radiating portion and the trocar helps ensure optimal performance of the microwave ablation probe. More specifically, it has been found that variation in the axial distance may result in a sub-optimal ablation shape, an irregular ablation zone, and/or degraded ablation performance. The various embodiments of probes and methods of manufacturing probes described in detail hereinbelow are configured to help eliminate this variation in axial distance, thereby facilitating optimal performance of the probe.

Turning now to FIGS. 1-7, a microwave ablation system provided in accordance with the present disclosure is shown generally identified by reference numeral 10. Microwave ablation system 10 includes a microwave antenna probe 12 configured to couple to a microwave generator (not shown) via a flexible coaxial cable 16. Although the present disclosure is shown and described with reference to a microwave ablation system 10, the present disclosure is equally applicable for use in determining and/or setting a particular distance between components of any suitable energy-based surgical instrument. For the purposes herein, microwave ablation system 10 is generally described.

With continuing reference to FIGS. 1-7, microwave antenna probe 12 generally includes an antenna assembly 20, an outer jacket and trocar assembly 70 and a connection hub 80. Antenna assembly 20 defines a longitudinal axis "X-X" and includes a radiating section that defines a dipole configuration, e.g., the radiating section includes a feed gap 43 and proximal and distal radiating portions 42, 44. A feedline 30 extends proximally from the radiating section into connection hub 80, ultimately coupling to cable 16 via transition 60 to connect antenna assembly 20 to the generator (not shown) for supplying energy thereto. Feedline 30 defines a coaxial configuration having an inner conductor 32 surrounded by an insulator 34. Insulator 34, in turn, is surrounded by an outer conductor 36, thus defining the coaxial configuration of feedline 30. Feedline 30 may be formed from a semi-rigid or flexible coaxial cable, although other configurations are also contemplated.

Figure 7:
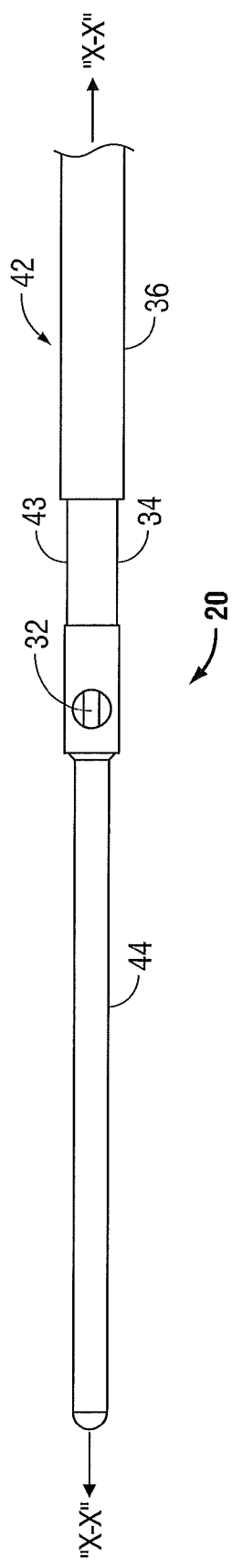
FIG. 7 is an enlarged view of the area of detail indicated as "7" in FIG. 6.

As mentioned above, and with reference to FIGS. 2, 4, and 6-7, the radiating section of antenna assembly 20 includes feed gap 43, proximal radiating portion 42, and distal radiating portion 44. Feed gap 43 is defined by the portion of inner conductor 32 and insulator 34 of feedline 30 that extends distally from outer conductor 36, e.g., outer conductor 36 may be stripped from the distal end of coaxial feedline 30 to define feed gap 43. Proximal radiating portion 42 is defined by the portion of feedline 30 disposed between the proximal end of feed gap 43 and the distal end of the choke 50. Distal radiating portion 44 is attached to feed gap 43 via any suitable process and extends distally therefrom. For example, as shown in FIG. 7, distal radiating portion 44 may be soldered to inner conductor 32 of feed gap 43 to establish electromechanical contact therebetween.

Antenna assembly 20, as shown in FIGS. 2, 4, and 6-7, further includes a choke or balun 50 disposed about feedline 30. Choke 50 includes an inner dielectric layer and an outer conductive layer. Choke 50 may be a quarter-wavelength shorted choke that is shorted to outer conductor 36 of feedline 30 at the proximal end of choke 50, although other configurations are contemplated. The dielectric layer of choke 50 may also be configured to extend distally beyond the conductor layer thereof towards the distal end of antenna assembly 20.

Figure 3:
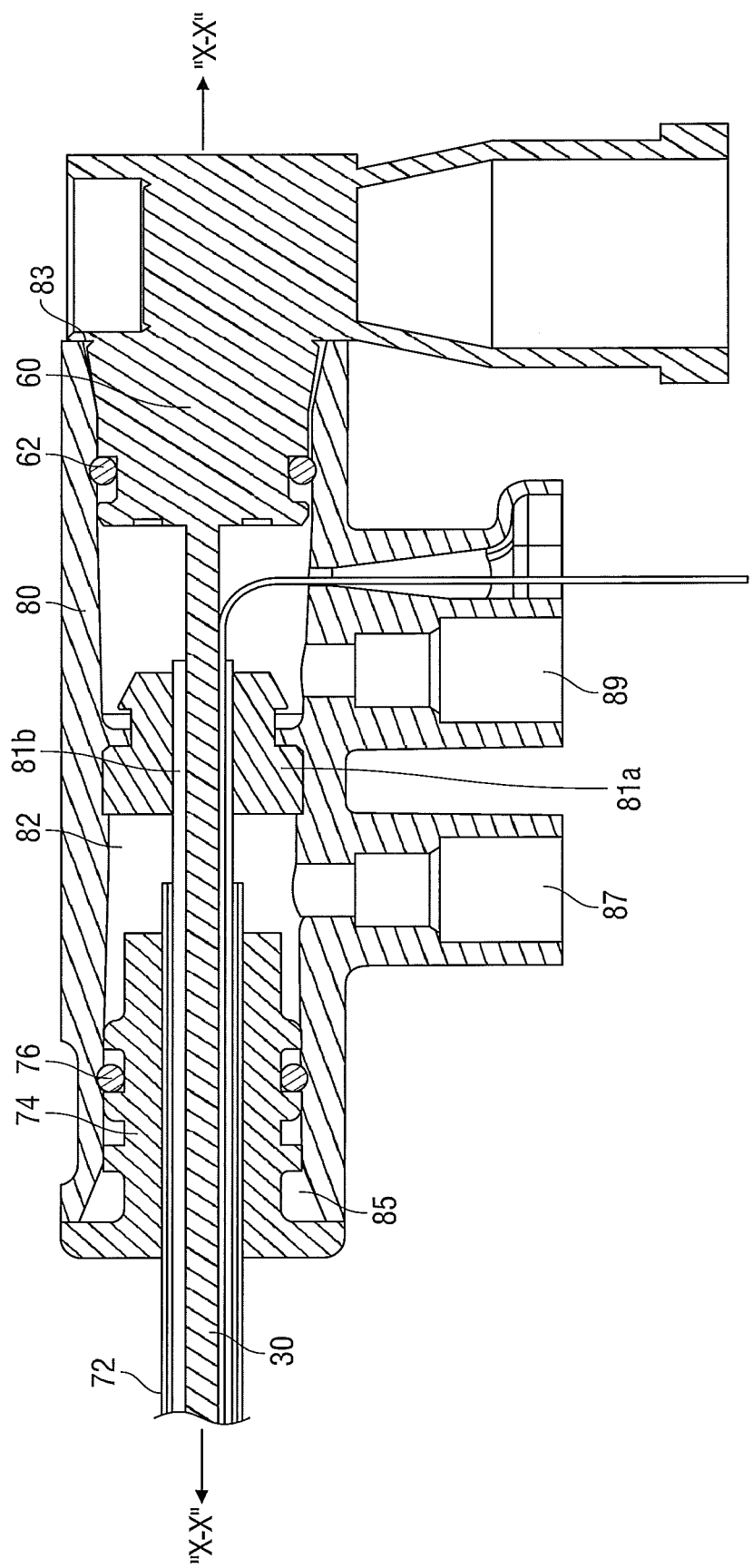
FIG. 3 is an enlarged view of the area of detail indicated as "3" in FIG. 2.

With additional reference to FIG. 3, as mentioned above, antenna assembly 20 includes a transition 60 from which feedline 30 extends. During assembly, the radiating section and feedline 30 of antenna assembly 20 are inserted through lumen 82 of connection hub 80, while transition 60 is inserted into proximal port 83 of connection hub 80 sufficiently such that transition 60 is sealingly engaged within proximal port 83 of connection hub 80 via O-ring 62. Feedline 30 extends into transition 60, wherein inner conductor 32 is coupled to an inner conductor (not explicitly shown) of coaxial cable 16 and outer conductor 36 is coupled to an outer conductor (not explicitly shown) of coaxial cable 16, while maintaining the spacing therebetween via an insulator (not explicitly shown). Cable 16 may be secured to feedline 30 within transition 60 via soldering, laser welding, or any other suitable process for establishing electromechanical contact therebetween.

Outer jacket and trocar assembly 70, as best shown in FIGS. 1-3 and 5, includes an outer jacket 72 configured to surround antenna assembly 20, e.g., proximal and distal radiating portions 42, 44, feed gap 43, and feedline 30, such that a coolant fluid may be circulated thereabout to maintain antenna assembly 20 in a relatively cooled state during use. More specifically, coolant fluid is pumped into lumen 82 of connection hub 80 to circulate through outer jacket 72 via supply tube 17 and inlet 87 and returns to the coolant fluid source (not shown) via outlet 89 and return tube 19. A ferrule 74 is molded or otherwise engaged about outer jacket 72 towards the proximal end thereof to facilitate sealing engagement of the proximal end of outer jacket 72 within distal port 85 of connection hub 80 via O-ring 76.

Connection hub 80, as mentioned above defines a longitudinal lumen 82 that is configured to receive feedline 30 therethrough, while sealingly engaging outer jacket 72 within distal port 85 and transition 60 within proximal port 83. Connection hub 80 further includes an outlet fluid port 87 and an inlet fluid port 89 that are disposed in fluid communication with lumen 82. Outlet and inlet ports 87, 89 are configured to receive tubes 17, 19 (see FIG. 1), respectively, such that, as mentioned above, coolant fluid from a coolant fluid supply (not shown) may be circulated through connection hub 80 and outer jacket 72. More specifically, an elastomeric (or otherwise configured) hub divider 81a is sealingly engaged within lumen 82 of connection hub 80 to isolate the inlet and outlet portions of lumen 82 of connection hub 80 from one another. Further, an inflow tube 81b is coupled to hub divider 81a and extends distally through outer jacket 72. As such, coolant fluid may flow from tube 17, through inlet port 87, into the inlet portion of lumen 82, and distally through inflow tube 81b, ultimately returning proximally through outer jacket 72 (exteriorly of inflow tube 81b), the outlet portion of lumen 82, outlet port 89, and into tube 19. This configuration allows for the circulation of coolant fluid about antenna assembly 20 to maintain antenna assembly 20 in a relatively cooled state during use. The coolant fluid may be a liquid, gas, other flowable material, or combination thereof.

Figure 4:
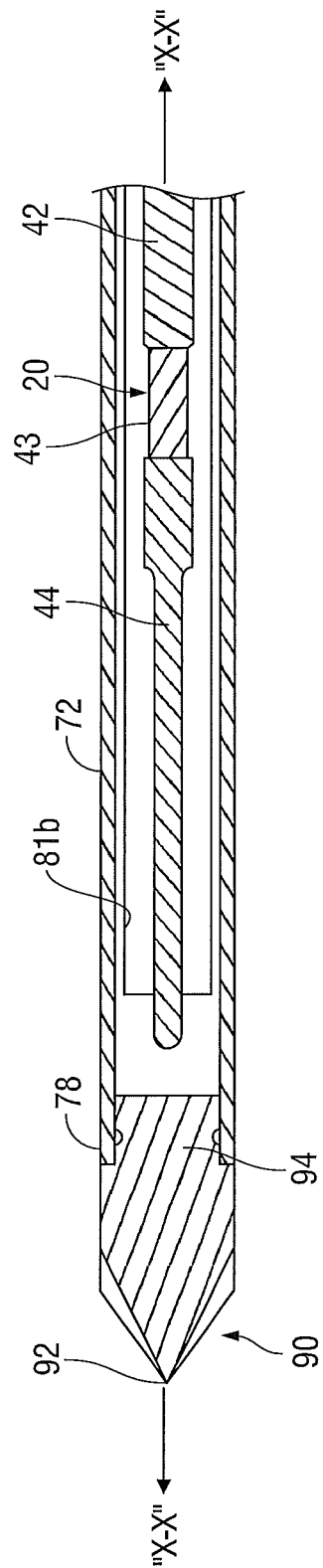
FIG. 4 is an enlarged view of the area of detail indicated as "4" in FIG. 2.
Figure 5:
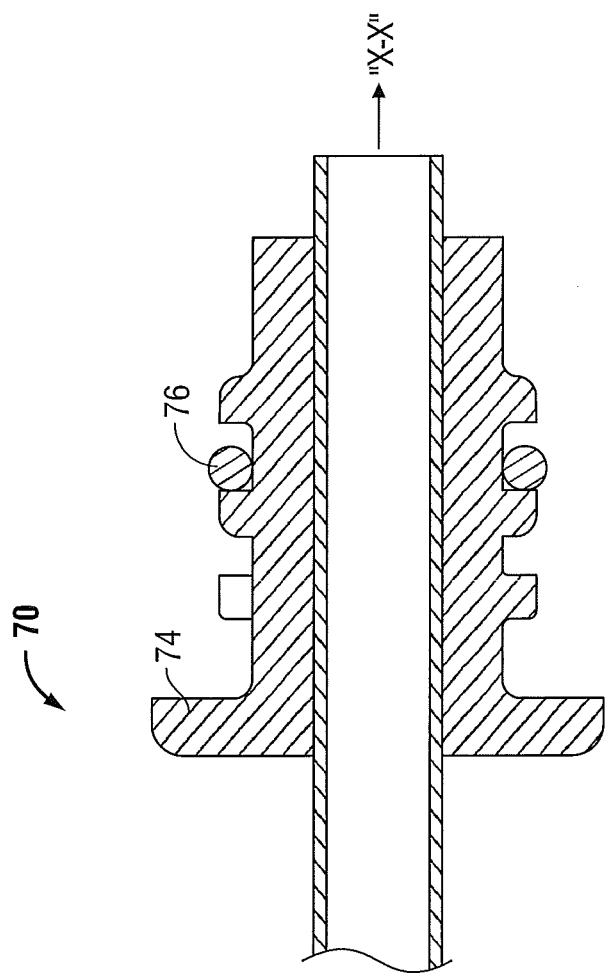
FIG. 5 is a longitudinal, cross-sectional view of an outer jacket and trocar assembly of the microwave antenna probe of FIG. 2.
Figure 5:
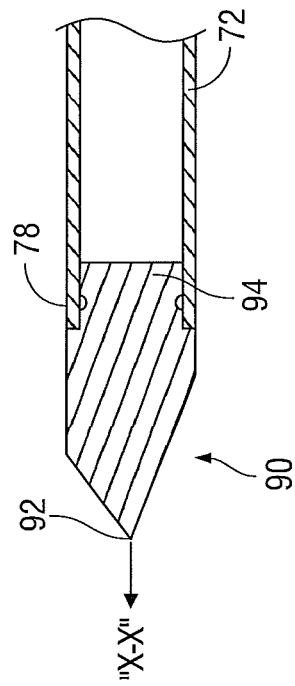
Figure 6:
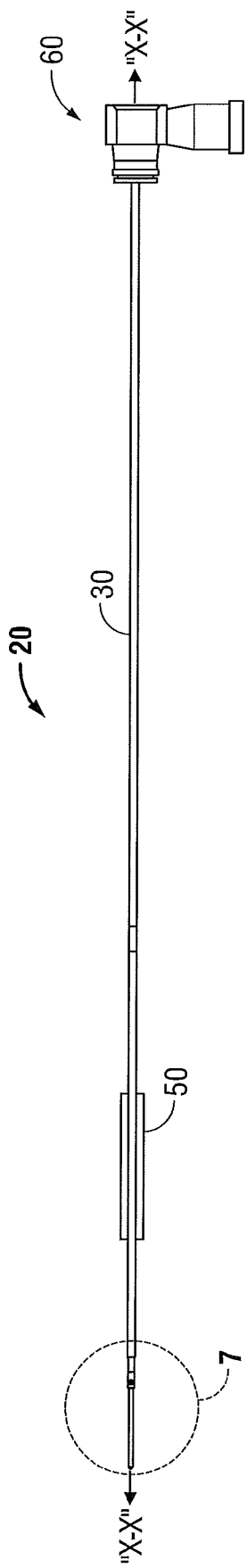
FIG. 6 is a side view of an antenna assembly of the microwave antenna probe of FIG. 2.

With reference to FIGS. 4-5, outer jacket and trocar assembly 70 further includes a trocar 90 defining a tapered distal end that terminates at a pointed distal tip 92 to facilitate insertion of microwave antenna probe 12 (FIG. 1) into tissue with minimal resistance, although other configurations may also be provided. Trocar 90 may be formed from a variety of heat-resistant materials suitable for penetrating tissue, e.g., metals (stainless steel, for example), various thermoplastic materials (such as polytherimide, polyimide thermoplastic resins, etc.), or any other suitable material. Base 94 of trocar 90 is configured for insertion into the open distal end 78 of outer jacket 72 for sealing engagement therein via any suitable process, e.g., using adhesives or via soldering. As such, trocar 90, once engaged within distal end 78 of outer jacket 72, sealingly encloses antenna assembly 20 (see FIG. 2) within outer jacket 72 and connection hub 80, thus defining an internal chamber for circulation of coolant fluid through microwave antenna probe 12 (FIG. 1) and inhibiting coolant fluid from leaking out of microwave antenna probe 12 during use. Trocar 90 may be secured to distal end 78 of outer jacket 72 prior to engagement of outer jacket and trocar assembly 70 to connection hub 80 and/or engagement of transition to connection hub 80, or may be secured to distal end 78 of outer jacket 72 after each of these assembly steps are complete.

Referring again to FIGS. 1-7, as mentioned above, it has been found that proper axial spacing between the distal end of distal radiating portion 44 of antenna assembly 20 and the proximal surface of base 94 of trocar 90 helps ensure optimal performance of microwave antenna probe 12. In particular, it has been found that, if the axial distance between the distal end of distal radiating portion 44 of antenna assembly 20 and the proximal surface of base 94 of trocar 90 is too large, the ablation zone, or ablation shape may be sub-optimal and complete ablation may not be readily achieved. Likewise, where the axial distance between the distal end of distal radiating portion 44 of antenna assembly 20 and the proximal surface of base 94 of trocar 90 is too small, or where distal radiating portion 44 and trocar 90 are in contact with one another, ablation performance may be degraded.

The optimal axial spacing, e.g., the target axial distance, between distal radiating portion 44 and trocar 90 depends on, among other things, the dimensions and configuration of microwave antenna probe 12, and may be determined empirically, experimentally, or in any other suitable fashion. Variation in the axial distance may result from: variation in the length of antenna assembly 20, e.g., due to variation in the attachment point of distal radiating portion 44 to inner conductor 32 and/or variation in the length or size of the individual components of antenna assembly 20; variation in the position of transition 60 and/or ferrule 74 relative to connection hub 82 and/or one another; variation in the distance trocar 90 extends from (or extends into) outer jacket 72 once engaged to outer jacket 72; variation in the axial position of ferrule 74 relative to outer jacket 72; and/or other factors, e.g., the particular manufacturing processes or materials used, the particular components used or relationship between the components, the configuration of the probe in general, etc.

With reference to FIG. 8, in accordance with one embodiment of the present disclosure, as will be described in greater detail below, electrical discharge may be utilized to help achieve the target axial distance between distal radiating portion 44 and trocar 90 during assembly, thereby facilitating optimal performance of microwave ablation probe 12.

With continued reference to FIG. 8, during assembly, once transition 60 is engaged within proximal port 83 of connection hub 80 via O-ring 62 and once ferrule 74 is engaged within distal port 85 of connection hub 80 via O-ring 76 such that antenna assembly 20, outer jacket 72, and connection hub 80 are secured in fixed position relative to one another, base 94 of trocar 90 is inserted into the open distal end 78 of outer jacket 72 for sealing engagement therein via any suitable process, e.g., using adhesives or via soldering. Since, at this point, outer jacket 72 and distal radiating portion 44 have already been fixed in position relative to one another, it is trocar 90 that is moved into a particular axial position corresponding to the target axial distance between the distal end of distal radiating portion 44 and the proximal surface of base 94 of trocar 90. Once in position, trocar 90 may be adhered, soldered, or otherwise engaged to outer jacket 72 at the particular axial position such that the target axial distance is achieved.

In order to determine when trocar 90 is properly positioned such that the target axial is achieved between trocar 90 and distal radiating portion 44 during assembly, trocar 90 is charged to a first voltage, while distal radiating portion 44 is charged to a second voltage that is different from the first voltage such that a pre-determined voltage differential is established between trocar 90 and distal radiating portion 44. As will be described below, the particular voltage differential between trocar 90 and distal radiating portion 44 may be selected in accordance with the target axial distance between distal radiating portion 44 and trocar 90, among other factors. Further, although FIG. 8 illustrates trocar 90 being charged to a greater voltage than distal radiating portion 44 such that trocar 90 is the anode, e.g., relatively positive "+," while distal radiating portion 44 is the cathode, e.g., relatively negative "−," this configuration may be reversed, e.g., wherein trocar 90 is the cathode and distal radiating portion 44 is the anode.

With the pre-determined voltage differential established between trocar 90 and distal radiating portion 44, trocar 90 may be advanced proximally relative to outer jacket 72 (and, thus distal radiating portion 44) such that base 94 of trocar 90 is inserted into the open distal end 78 of outer jacket 72. While monitoring the respective voltages of trocar 90 and distal radiating portion 44 (and/or the voltage differential therebetween), trocar 90 is advanced further proximally relative to distal radiating portion 44, e.g., further into open distal end 78 of jacket 72, until electrical discharge occurs between trocar 90 and distal radiating portion 44, as evidenced by change in voltages of trocar 90 and distal radiating portion 44 or a decrease in the voltage differential therebetween. When discharge occurs, the target axial distance between the distal end of distal radiating portion 44 and the proximal surface of base 94 of trocar 90 has been achieved. More specifically, the pre-determined voltage differential is set in accordance with the target axial distance such that discharge occurs once trocar 90 and distal radiating portion 44 are spaced-apart by the target axial distance. Once this target axial distance is achieved, e.g., once discharge occurs, the supply of voltage to trocar 90 and distal radiating portion 44 may be terminated, and trocar 90 may be engaged to outer jacket 72 at that particular position, thereby establishing the target axial distance between trocar 90 and distal radiating portion 44.

As mentioned above, the voltage differential between trocar 90 and distal radiating portion 44 is set such that the distance between trocar 90 and distal radiating portion 44 at which discharge occurs corresponds to the target axial distance between trocar 90 and distal radiating portion 44. The particular relationship between the voltage differential and the distance at which discharge occurs may be determined experimentally, empirically, or in any other suitable fashion, such that an appropriate voltage differential may be established. Further, the above-described process may be automated, e.g., using robotics or other automated or semi-automated assembly processes, such that trocar 90 is advanced, e.g., incrementally at a pre-determined step size or continuously at a pre-determine rate, until discharge occurs, whereby feedback as to the occurrence of discharge is provided to stop further movement of trocar 90 and maintain trocar 90 in position such that trocar 90 may be engaged to outer jacket 72 at that position, thereby achieving the target axial distance between trocar 90 and distal radiating portion 44. Any of the other embodiments described herein may similarly be incorporated into an automated or semi-automated feedback system, as described above.

As opposed to using the occurrence of electrical discharge to determine when proper axial spacing between trocar 90 and distal radiating portion 44 has been achieved, a resistivity or conductivity sensor (see, e.g., sensor assembly 300 (FIG. 11)), may be used in conjunction with the voltage differential between trocar 90 and distal radiating portion 44 to determine the axial spacing between trocar 90 and distal radiating portion 44. More specifically, with trocar 90 and distal radiating portion 44 immersed in a conductive fluid, e.g., a conductive gas or liquid, having a known conductivity or resistivity, and with the pre-determined voltage differential established between trocar 90 and distal radiating portion 44, the known conductivity or resistivity of the fluid, along with the known voltage differential between trocar 90 and distal radiating portion 44, can be used to determine the axial spacing between trocar 90 and distal radiating portion 44 based upon the sensed conductivity or resistivity between the charged components, e.g., trocar 90 and distal radiation portion 44. This is because the sensed conductivity or resistivity between the charged components is dependent upon the conductivity or resistivity of the fluid, the distance between the charged components, and the voltage differential between the charged components. Thus, working backwards from the known conductivity or resistance of the fluid and the voltage differential between the charged components, the distance therebetween can be determined. A controller/processor (see, e.g., controller/processor 320 (FIG. 11)) may be utilized in conjunction with the resistivity or conductivity sensor to determine and display or provide feedback as to the axial spacing between trocar 90 and distal radiating portion 44.

Turning now to FIG. 9, in accordance with another embodiment of the present disclosure, a sensing member 200 may be utilized to achieve the target axial distance between trocar 90 and distal radiating portion 44 during assembly. Sensing member 200 is disposed within lumen 82 of connection hub 80 and, more particularly, is disposed with outer jacket 72. Sensing member 200 is electrically coupled to a controller/processor 210 via one or more wires 220. Sensing member 200 may be permanently affixed within connection hub 80 and outer jacket 72, or may be removably disposed therein such that, once trocar 90 is moved into position and engaged to distal end 78 of outer jacket 72, sensing member 200 may be withdrawn from outer jacket 72 and connection hub 80. Further, sensing member 200 may be disposed at any suitable position within outer jacket 72, e.g., in a more distal position towards distal radiating portion 44, within connection hub 80 (as shown), or at any suitable position therebetween. The particular positioning of sensing member 200, as can be appreciated, may depend of the particular type of sensing member used.

Sensing member 200 may be in the form of an acoustic transmitter/receiver configured to emit, via the transmitter, a pre-determined acoustic signal distally into outer jacket 72 and to detect the acoustic response via the receiver. The acoustic response, which is correlated to the axial distance between the distal end of distal radiating portion 44 and the proximal surface of base 94 of trocar 90, may thus be used to determine the axial distance between trocar 90 and radiating portion 44. More specifically, the acoustic response detected by the receiver of the acoustic transmitter/receiver is transmitted to controller/processor 210, which analyzes the response to determine the distance between trocar 90 and distal radiating portion 44. Alternatively, the response may be compared to a target response value, e.g., the response value corresponding to the target axial distance between trocar 90 and distal radiating portion 44, that is stored in controller/processor 210. In such a configuration, the controller/processor 210 determines whether the trocar 90 is in proper position by determining whether or not the responses value match (or are sufficiently similar). If a match is determined, trocar 90 is in the proper position wherein trocar 90 and distal radiating portion 44 are spaced-apart by the target axial distance. Comparison of the sensed response value to the target response value may also be used to determine whether trocar 90 and distal radiating portion 44 are too close or too far from one another, thus indicating the required direction of movement of trocar 90 to achieve the target axial distance between trocar 90 and distal radiating portion 44.

The particular relationship between the response values sensed by sensing member 200 and the axial distance between trocar 90 and distal radiating portion 44 may be determined experimentally, empirically, or in any other suitable fashion. Further, similarly as described above with respect to the previous embodiment, sensing member 200 and controller/processor 210 may be incorporated into an automated, feedback-based system. Other suitable sensing members, e.g., piezoelectric sensors, optical sensors, or any other suitable sensor for determining the distance between trocar 90 and distal radiating portion 44, may also be used.

Figure 10:
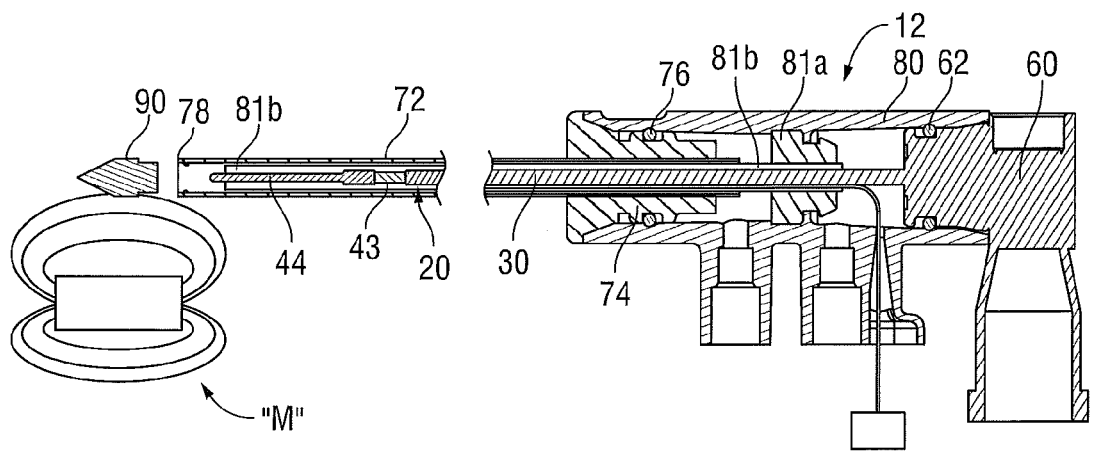
FIG. 10 is a longitudinal, cross-sectional view illustrating assembly of the microwave antenna probe of FIG. 2 in accordance with other aspects of the present disclosure.

With reference to FIG. 10, in accordance with another embodiment of the present disclosure, a magnetic field "M,"

multiple magnetic fields, changing magnetic field(s), etc., may be selectively applied to microwave antenna probe 12 to determine the positioning of trocar 90 and distal radiating portion 44 relative to one another such that trocar 90 may be moved into position to achieve the target axial distance between trocar 90 and distal radiating portion 44. More specifically, by analyzing the magnetic field(s) "M," the various components of microwave antenna probe 12 and the relative positioning therebetween can be determined since the magnetic field(s) "M" exhibits different characteristics adjacent the different components, e.g., adjacent trocar 90 and distal radiation portion 44. Accordingly, while monitoring the magnetic field(s) "M," and, thus, while monitoring the axial spacing between trocar 90 and distal radiating portion 44, trocar 90 may be moved into position to achieve the target axial distance between trocar 90 and distal radiating portion 44. Once this target axial distance is achieved, trocar 90 may be engaged to outer jacket 72 at the proper position to retain trocar 90 in fixed position relative to distal radiation portion 44. An appropriate magnetic field(s) "M" may also be applied to retain trocar 90 in position during engagement of trocar 90 to outer jacket 72, thereby obviating the need to mechanically retain trocar 90 in position.

Figure 11:
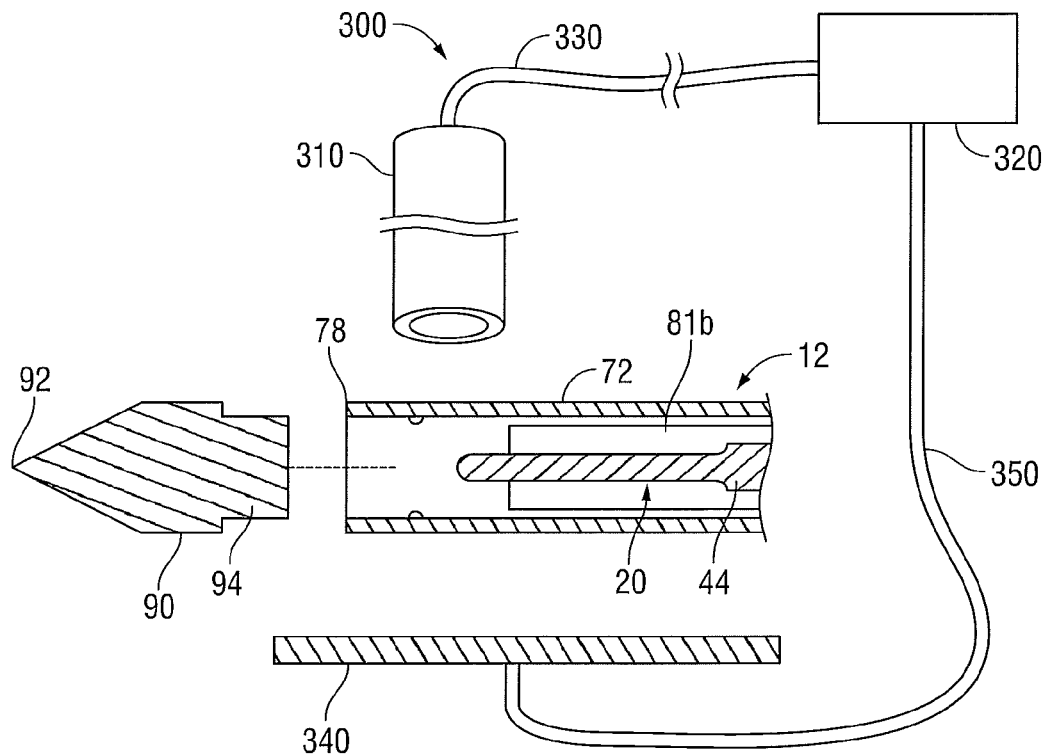
FIG. 11 is an enlarged, longitudinal, cross-sectional view of a distal end of the microwave antenna probe of FIG. 2 illustrating assembly of the microwave antenna probe in accordance with other aspects of the present disclosure.

Referring to FIG. 11, in accordance with another embodiment of the present disclosure, an external sensor assembly 300 may be utilized to achieve the target axial distance between distal radiating portion 44 and trocar 90 during assembly. External sensor assembly 300 is a contactless sensor disposed exteriorly of microwave antenna probe 12 and is configured to determine the axial distance between trocar 90 and distal radiating portion 44 without the need to contact either trocar 90 or distal radiating portion 44 (or any other portion of microwave antenna probe 12). Thus, trocar 90 may be moved into position in accordance with the feedback, e.g., the axial distance between trocar 90 and distal radiating portion 44, obtained from sensor assembly 300 without being inhibited by sensor assembly 300. Sensor assembly 300 may include cooperating components 310, 340, e.g., an emitter 310 and a detector 340, although the particular configuration of components 310, 340 may depend on the particular type of sensor assembly used, that are coupled to a controller/processor 310 via one or more wires 320, 350, respectively. Controller/processor 310 is configured to analyze the response from sensor components 310, 340 to determine the axial spacing between trocar 90 and distal radiating portion 44.

Sensor assembly 300 may be in the form of a capacitive proximity sensor, an inductive (eddy current) proximity sensor, a magnetic proximity sensor, or any other suitable external contactless sensor configured to emit a signal and receive a response for determining the axial spacing between trocar 90 and distal radiating portion 44. More specifically, in use, after emission of a signal, application of an energy field, or other excitation by sensor component 310 and/or sensor component 340, the response(s) received by sensor component 310 and/or sensor component 340 is sent to controller/processor 310, which analyzes the response to determine the axial distance between trocar 90 and distal radiating portion 44. Using this feedback, trocar 90 may be accurately positioned relative to distal radiating portion 44.

For example, with respect to a capacitive proximity sensor, capacitance, e.g., capacitance sensed by sensor assembly 300, can be used to determine the axial distance between trocar 90 and distal radiating portion 44 since capacitance is dependent upon the distance between the components, e.g., trocar 90 and distal radiating portion 44. With respect to an inductive proximity sensor, since inductance is likewise dependent on distance, an inductive proximity sensor can be used to determine the axial distance between trocar 90 and distal radiating portion 44, the difference being that capacitive proximity sensors utilize electrical capacitance, while inductive proximity sensors utilized magnetic inductance.

Referring in general to FIGS. 1-11, the above-described embodiments provide for accurate placement of trocar 90 relative to distal radiating portion 44 despite variation among the individual components of microwave antenna probe 12 or the engagements therebetween, e.g., without the need to rely on the accuracy of the dimensions, positioning, or engagement of the other components. That is, placement of trocar 90 relative to distal radiating portion 44 as described above is accomplished irrespective of variation among the components, e.g., variations in length, relative positioning, and/or configuration of one or more of the components. Accordingly, accurate positioning of trocar 90 relative to distal radiating portion 44 can be readily achieved, thereby helping to ensure optimal performance.

Although the assembly of microwave ablation probe 12 is described above wherein trocar 90 is engaged to outer jacket 72 once transition 60 has been engaged within proximal port 83 of connection hub 80 via O-ring 62 and engagement of ferrule 74 within distal port 85 of connection hub 80 via O-ring 76, it is also contemplated that above-described assembly methods may similarly be performed wherein the engagement of transition 60 to connection hub 80 or the engagement of outer jacket 72 to connection hub 80 is performed once the other components are fixed relative to one another. For example, with trocar 90 engaged to outer jacket 72 and transition 60 engaged within proximal port 83 of connection hub 80, any of the above-described embodiments may be utilized to guide the positioning and engagement of ferrule 74 within distal port 85 of connection hub 80 such that the target axial spacing between trocar 90 and distal radiating portion 44 is achieved. Likewise, with trocar 90 engaged to outer jacket 72 and ferrule 74 engaged within distal port 85 of connection hub 80, any of the above-described embodiments may be utilized to the guide the positioning and engagement of transition 60 within proximal port 83 of connection hub 80 such that the target axial spacing between trocar 90 and distal radiating portion 44 is achieved.

Although the various embodiments above are described with respect to determining the spacing between trocar 90 and distal radiating portion 44 during assembly of trocar 90 to outer jacket 72, it is also contemplated that any or all of the above-described embodiments may be used to record, mark, or otherwise note the proper positioning of trocar 90 (and/or the other components of microwave ablation probe 12) such that, upon subsequent assembly, trocar 90 (and/or the other components) may be positioned in accordance with the recorded, marked, or otherwise noted position previously obtained. As such, proper positioning of trocar 90 (and/or the other components) can be readily achieved. Alternatively or additionally, the above-described embodiments may be utilized for quality control, e.g., to ensure that the target axial distance between trocar 90 and distal radiating portion 44 has been achieved once assembly has been completed.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodi-

What is claimed is:

1. A method of manufacturing a surgical instrument, comprising:
   charging a first component to a first voltage;
   charging a second component to a second voltage such that a pre-determined voltage differential is established between the first and second components;
   axially moving at least one of the first and second components relative to the other;
   monitoring an electrical characteristic to determine whether an axial distance between the first and second components is equal to a target axial distance; and
   retaining the first and second components in fixed position relative to one another once the axial distance between the first and second components is equal to the target axial distance.

2. The method according to claim 1, wherein the voltage differential between the first and second components is monitored to determine whether electrical discharge has occurred, and wherein, when electrical discharge occurs, the axial distance between the first and second components is equal to the target axial distance.

3. The method according to claim 2, wherein a decrease in the voltage differential between the first and second components indicates the occurrence of electrical discharge between the first and second components.

4. The method according to claim 2, wherein the pre-determined voltage differential is selected in accordance with the target axial distance between the first and second components.

5. The method according to claim 1, wherein one of conductivity and resistivity between the first and second components is monitored to determine the axial distance between the first and second components.

6. The method according to claim 5, further comprising the step of immersing the first and second components in a fluid having one of pre-determined conductivity and pre-determined resistivity, wherein the voltage differential between the first and second components, the one of pre-determined conductivity and pre-determined resistivity, and the monitored one of conductivity and resistivity between the first and second components, are used to determine the axial distance between the first and second components.

7. The method according to claim 1, wherein the target axial distance is determined one of empirically and experimentally.

8. The method according to claim 1, wherein the surgical instrument includes a microwave probe having a radiating portion and a trocar, the radiating portion and the trocar configured to be spaced-apart by the target axial distance.

9. The method according to claim 1, wherein the steps of axially moving the at least one of the first and second components, monitoring the electrical characteristic, and retaining the first and second components, are incorporated into an automated feedback system.

10. A method of manufacturing a microwave probe comprising:
    providing a radiating probe and a trocar
    axially moving at least one of the radiating probe or the trocar relative to the other;
    sensing a characteristic of energy to determine whether an axial distance between the radiating probe and the trocar is equal to a target axial distance; and
    retaining the radiating probe and the trocar in fixed position relative to one another once the axial distance between the radiating probe and the trocar is equal to the target axial distance.

11. The method according to claim 10, wherein one of capacitance or inductance between the radiating probe and the trocar is sensed to determine the axial distance between the radiating probe and the trocar.

12. The method according to claim 10, where at least one magnetic field is applied to the microwave probe, and wherein characteristics of the magnetic field are sensed to determine the axial distance between the radiating probe and the trocar.

13. The method according to claim 10, wherein an acoustic response is sensed to determine whether the axial distance between the radiating probe and the trocar is equal to the target axial distance.

14. The method according to claim 13, wherein the acoustic response is sensed in response to an acoustic excitation signal emitted generally towards the radiating probe and the trocar.

15. The method according to claim 10, wherein the target axial distance is determined either empirically or experimentally.

16. The method according to claim 10, wherein axially moving the at least one of the radiating probe and the trocar, sensing the characteristic of energy, and retaining the radiating probe and trocar, are incorporated into an automated feedback system.

* * * * *